United States Patent
Weaver et al.

(10) Patent No.: US 6,869,194 B2
(45) Date of Patent: Mar. 22, 2005

(54) STERILIZABLE DRAPE FOR OPHTHALMOSCOPIC LENS

(75) Inventors: Richard A. Weaver, Fenton, MI (US); Joseph M. Wright, Fenton, MI (US); Nathan M. Sokolowski, Fenton, MI (US)

(73) Assignee: Contour Fabricators, Inc., Fenton, MI (US)

( * ) Notice: Subject to any disclaimer, the term of this patent is extended or adjusted under 35 U.S.C. 154(b) by 32 days.

(21) Appl. No.: 10/395,670

(22) Filed: Mar. 24, 2003

(65) Prior Publication Data

US 2004/0190139 A1 Sep. 30, 2004

(51) Int. Cl.⁷ .......................... G02B 21/00; A61B 19/02
(52) U.S. Cl. ...................................... 359/510; 383/907
(58) Field of Search ................................. 359/510, 511; 206/466, 471; 383/902, 907

(56) References Cited

U.S. PATENT DOCUMENTS

| | | | | |
|---|---|---|---|---|
| 4,799,779 A | * | 1/1989 | Mesmer ...................... | 359/510 |
| 5,122,904 A | * | 6/1992 | Fujiwara et al. ............ | 359/510 |
| 5,608,574 A | * | 3/1997 | Heinrich ...................... | 359/510 |
| 6,024,454 A | | 2/2000 | Horan et al. | |
| 6,116,741 A | * | 9/2000 | Paschal ...................... | 359/510 |
| 6,318,864 B1 | * | 11/2001 | Fukaya et al. .............. | 359/510 |
| 6,459,538 B2 | * | 10/2002 | Grafenhain ................. | 359/808 |
| 2002/0151848 A1 | * | 10/2002 | Capote et al. .............. | 604/171 |

* cited by examiner

Primary Examiner—John Juba, Jr.
(74) Attorney, Agent, or Firm—John K. McCulloch

(57) ABSTRACT

A sterile drape for enclosing an ophthalmoscopic lens housing projecting from a surgical microscope has a wall defining a chamber of such size as to accommodate the lens housing and supporting parts. The chamber communicates with a compartment in which the lens housing may be accommodated and supported in an appropriate position. The compartment has transparent plates at its opposite ends and the chamber wall adjacent the opening has a circular lens which may underlie a microscope. The compartment plates and the circular lens enable the image to be transmitted from a surgical site without distortion while maintaining a sterile environment at such site.

14 Claims, 4 Drawing Sheets

STERILIZABLE DRAPE FOR OPHTHALMOSCOPIC LENS

This invention relates to a sterilizable drape adapted to enclose an ophthalmoscopic lens which is used in conjunction with an operating microscope in the performance of neurology and ophthalmology surgical procedures.

BACKGROUND OF THE INVENTION

In the performance of some surgical procedures an operating microscope has attached thereto a housing containing an ophthalmoscopic lens, for example, and prisms for orienting properly the image of the surgical field. The housing normally is one which cannot be subjected to conventional sterilizing procedures. Consequently, the lens housing must be enclosed within a sterile drape. A drape of the kind currently in use with apparatus of the type referred to comprises a boot which is small in size and fits closely the lens housing. As a consequence, it is very difficult to apply the drape without touching the non-sterile housing, thereby compromising the sterility of the surgical environment or requiring several attempts to place a sterilized boot over the housing.

A principal object of the invention is to facilitate the sterile draping of lens and prism housings of the general class described.

SUMMARY OF THE INVENTION

A sterilizable drape according to the invention comprises a pouch of pliable, sterilizable material forming a chamber having an opening at one end, but otherwise being closed. The opening is gathered at its edge so as to enable its area to be expanded and contracted. A stretchable, annular support is secured to the pouch adjacent the opening to enable the opening to accommodate and pass an adapter on the microscope so that the pouch may be suspended from the microscope.

The pouch has a wall which defines the chamber and is of such size as to accommodate freely the lens/prisms housing and its support parts. Protruding from the chamber is a compartment of such size as snugly to accommodate a portion of the lens housing. Opposite ends of the compartment are closed by transparent plates which facilitate the passage of light through the compartment from one end to the other.

That portion of the pouch between the compartment and the annular support is stiffened by a quadrangular strip and that portion of the wall of the pouch between the stiffener and the annular support is stiffened by a circular lens which is adapted to underlie the microscope. The circular lens is maintained in proper position relative to the microscope by separable fasteners which react between the interior of the pouch and the microscope.

The construction and arrangement of the parts are such that an image from the surgical site passes into the ophthalmoscopic lens through the lower lens of the compartment, is oriented by the prisms, and passes through the upper lens of the compartment into the microscope. The quadrangular stiffener ensures that no part of the pouch wall lies in the image path between the surgical site and the microscope.

THE DRAWINGS

Apparatus constructed in accordance with the presently preferred embodiment of the invention is disclosed in the accompanying drawings in which.

THE PREFERRED EMBODIMENT

Figure 2:
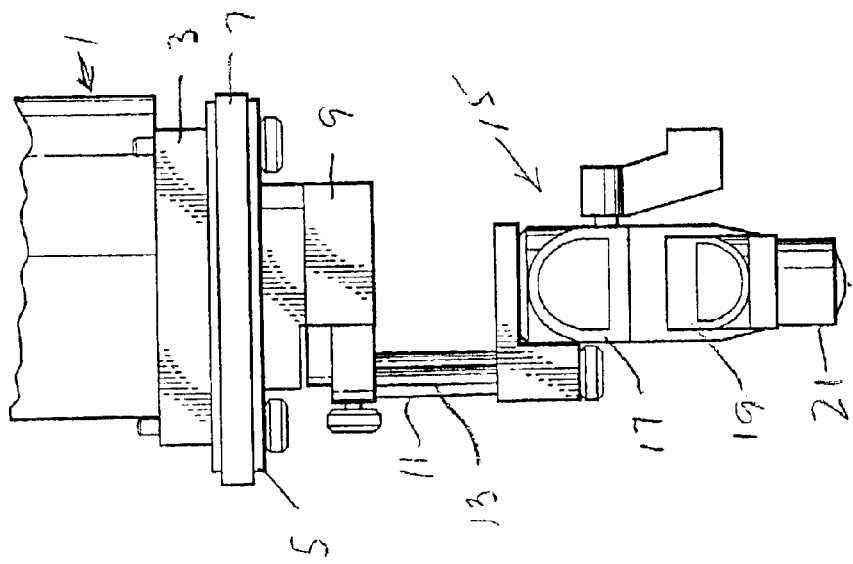
FIG. 2 is a front elevational view of such apparatus.
Figure 1:
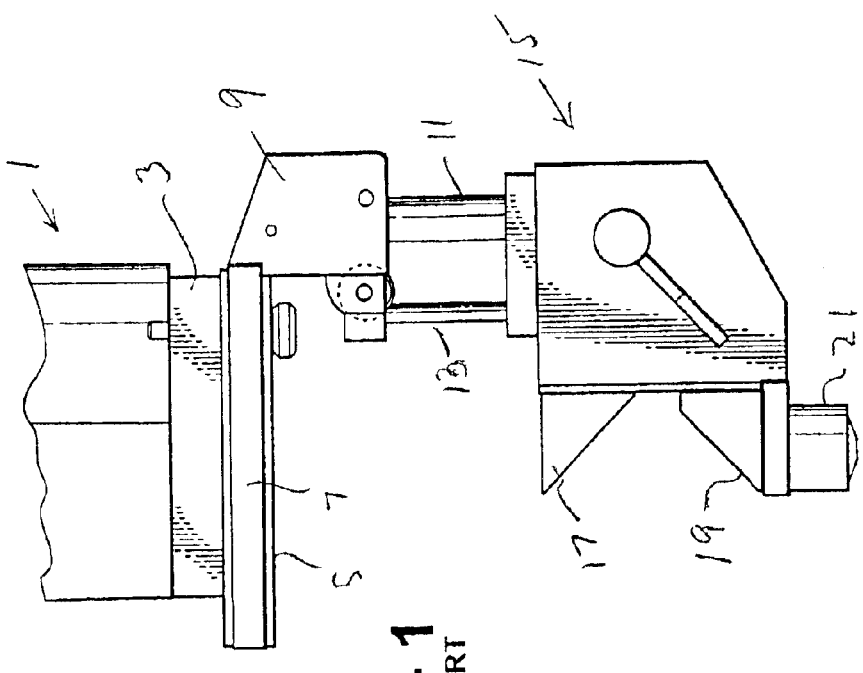
FIG. 1 is a side elevational view of known apparatus with which the invention may be used.

Apparatus constructed in accordance with the invention is adapted for use with a conventional operating microscope 1 of the kind used in neurological and ophthalmological surgical procedures. The microscope 1 as disclosed herein corresponds to an Ophtamic 900 operating microscope available from J. D. Moller Optische Werke GmbH of Wedel, Germany. Such a microscope has a depending lens housing 3 to which is secured an adapter ring 5 which forms a radially outward extending flange 7. Secured to the flange 7 is a mounting bracket 9 from which extends a suspension rod 11 and a guide rod 13. A housing 15 is supported and suspended from the rods 11 and 13. From the housing protrudes a pair of vertically spaced prism supports 17 and 19. Secured to the lower support 19 is a holder 21 for lenses.

The housing 15 and its associated parts are so arranged that an image from a surgical site below the lens holder 21 may traverse a path to the microscope 1 via the lens holder 21 and the prisms supported by the housing 15.

The apparatus suspended from the microscope 1 and described thus far is available from Moller Wedel, of Wedel, Germany, and is identified as Model Eibos 200. The apparatus thus far described forms no part of the invention other than in the manner in which it cooperates with the apparatus yet to be described.

When using the apparatus referred to above in the performance of a surgical procedure the lens holder 21 and its support structure must be positioned very close to the surgical site. It is essential, therefore, that such parts be enclosed in a sterile environment. Sterility is achieved according to the invention by the use of a sterile pouch 23.

The pouch 23 has a thin, durable, pliable wall 25 formed of sterilizable material, such as polyethylene or a suitable vinyl. The wall defines a chamber 27 and preferably is transparent to facilitate an attendant's being able to see through the wall into the chamber 27. However, transparency of the entire wall is not essential.

The chamber is closed except for an opening 29 at one end of the pouch. The edge of the wall material adjacent the opening is gathered in a conventional manner to enable the area of the opening to be expanded and contracted. The edge of the wall adjacent the opening is secured to an elastically stretchable, annular support 31 formed of a suitable material such as foamed polyethylene. The elasticity of the material forming the support 31 makes it possible for the support to be stretched, thereby temporarily expanding the area of the opening 29 into the chamber 27, and enabling the adapter ring 5 to pass through the opening 32, following which the support ring 31 may be released whereupon the area of the opening will contract and enable the pouch to be suspended from the ring 5 of the microscope 1.

Adjacent the lower end of the pouch wall 25 is secured a trough-shaped compartment 33 formed of glass or a suitable plastic. The compartment has a semi-circular wall 35 joined at its opposite ends to planar extensions 37. The compartment projects through an opening 39 in the wall. The compartment extensions 37 seat on the chamber wall 25 and seal the opening 39. At opposite ends of the compartment 33 are planar, coaxial, preferably transparent lenses or plates 42 formed of glass or a suitable plastic material.

The compartment 33 is of such height and width as snugly to accommodate therein the prism housings 17 and 19 and the lens holder 21. At the lower end of the compartment is a step-forming flange 43 which forms a socket to accommodate the lens holder 21. The arrangement is such that the components 17, 19, and 21, as well as a portion of the housing 15, will be securely, but removably, accommodated and retained within the compartment.

Adjacent the upper end of the compartment 33 the chamber wall 25 is reinforced by a quadrangular stiffening strip 44 of glass or polypropylene for a purpose presently to be explained. Between the reinforcement 44 and the opening 29 the chamber wall 25 supports a circular stiffening lens 46 of transparent glass or polypropylene. The position and area of the lens 46 are such that the lens 46 corresponds in area to that of the ring 5, and the volume of the chamber is sufficient to enable the lens 46 to be moved to a position in which it underlies and parallels the ring 5. The reinforcement strip 44 may be maintained in such position by cooperating hook and loop retainers 48 and 50, the retainer 48 being adhered to one face of the bracket 9 and the retainer 50 being adhered to the inner surface of the chamber wall 25.

To condition the apparatus for use the pouch 23, with the support ring 31 uppermost, is placed beneath the housing 15 and the lens 21. An attendant, wearing sterile gloves, will be able to move the pouch upwardly by grasping the support ring 31, thereby enabling the housing 15 and its associated parts to pass through the opening 29 and be accommodated within the chamber 27. The attendant may stretch the support ring 31 so as to expand the area of the opening sufficiently to enable the support ring to pass over the adapter ring 5, whereupon the attendant may relax the support ring 31 thereby enabling it to contract and reduce the area of the opening into the chamber. In its relaxed condition, the support ring will overlie the upper surface of the adapter ring 5 and enable the pouch to be suspended therefrom.

Following coupling of the pouch to the microscope the compartment 33 may be manipulated in such manner as to cause the prism supports 17 and 19 and the lens holder 21, along with a portion of the housing 15, to be accommodated in the compartment. The opening between the chamber 27 and the interior of the compartment 33 is such that the lens holder 21 will pass into the compartment first, following which the compartment may be rocked to position the lens adjacent the lower compartment plate 42. Thereafter, the remainder of the housing parts may be accommodated in the compartment where they will be retained snugly.

Following the fitting of a part of the housing 15 into the compartment 33 that portion of the wall 25 which carries the stiffening lens 46 may be moved upwardly to a position in which the lens 46 underlies and parallels the adapter ring 5. This position of the lens may be maintained by engaging the cooperable retainer components 48 and 50.

Figure 3:
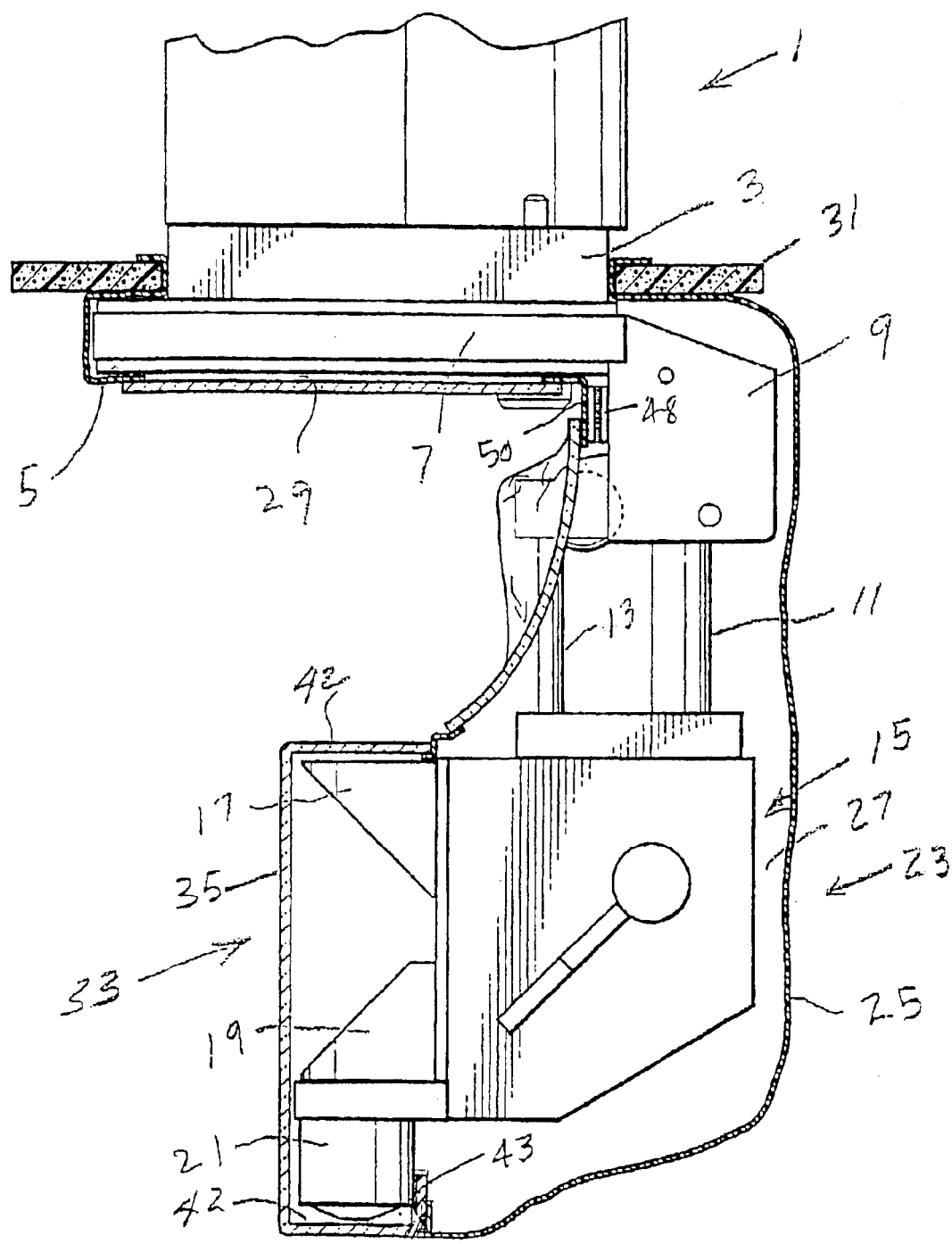
FIG. 3 is a fragmentary, side elevational view of part of a microscope to which is attached a housing containing an ophthalmoscopic lens and prisms, such housing being enclosed by a sterile pouch.
Figure 4:
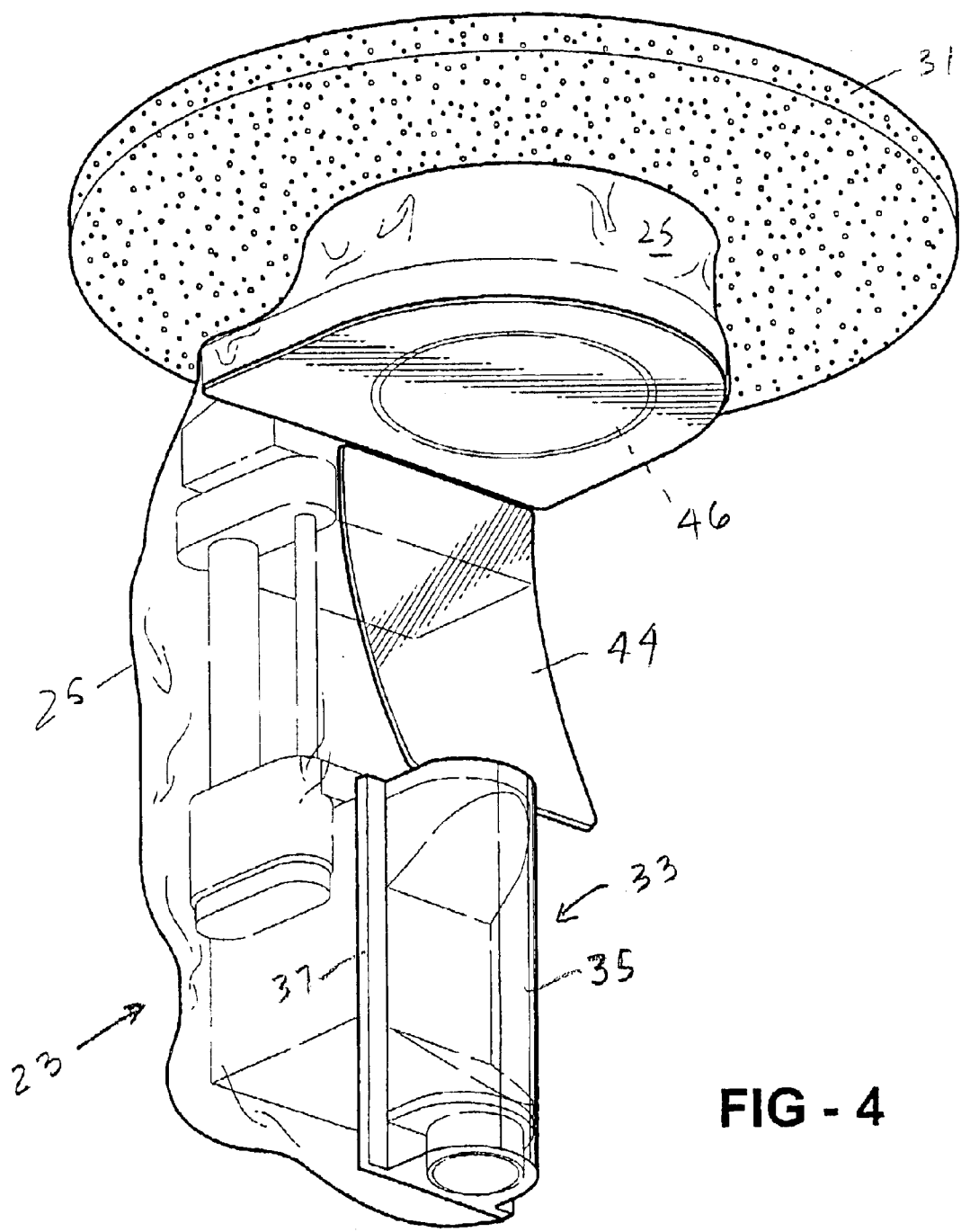
FIG. 4 is an isometric view of the apparatus shown in FIG. 3.
Figure 5:
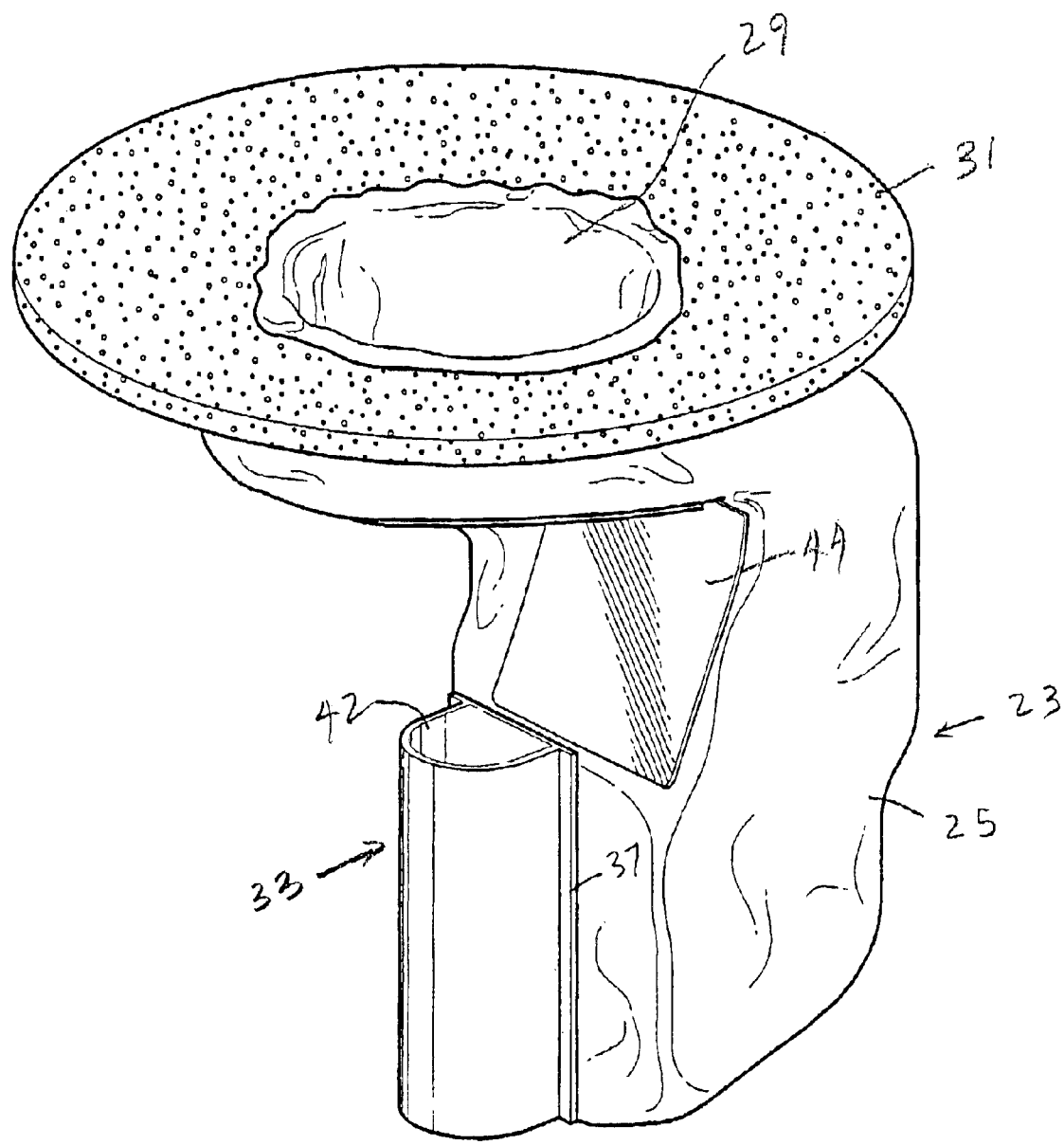
FIG. 5 is an isometric view similar to FIG. 4, but from a different direction.

Since the material forming the chamber wall 27 is pliable and since the volume of the chamber 25 must be sufficient to accommodate the housing 15 and its associated parts, there is some possibility that the portion of the wall 25 between the compartment 33 and the lens 46 may sag or blouse and obstruct the passage of light from the upper plate 42 of the compartment to the microscope 1. It is for this reason that the chamber wall 27 in the zone between the compartment 33 and the lens 46 is reinforced by the reinforcement 44. When the parts are in the positions shown in FIGS. 3 and 4, the reinforcement 44 will be inclined upwardly and resist sagging of the chamber wall.

Following application of the pouch to the microscope an image of a surgical site may be transmitted via the lens holder 21, the prisms 19 and 17, and through the transparent plates 42 directly to the microscope 1. Since the plates 42 and the lens 46 are planar there will be no distortion of the transmitted image.

Because of the relatively large volume of the pouch chamber and the width of the annular support ring 31 the housing 15 and its associated parts easily may be enclosed within a sterile environment.

A surgeon looking through the microscope at the surgical site will be able to view the area outside and on opposite sides of the compartment 33. As a consequence the movement of a surgical tool toward the surgical site may be observed.

The disclosed embodiment is representative of a presently preferred form of the invention, but is intended to be illustrative rather than definitive thereof. The invention is defined in the claims.

We claim:

1. A sterilizable drape apparatus for enclosing an ophthalmoscopic lens housing projecting from and beyond a surgical microscope having an adapter for coupling said lens housing to said microscope, said apparatus comprising a pouch having an opening at one end and forming an otherwise closed chamber; an elastic stretchable pouch support for coupling said pouch to said adapter, said support being secured to said pouch at said one end thereof and when in a relaxed condition reducing the area of said opening to one disabling said adapter from passing through said opening; and a compartment carried by and projecting beyond said pouch at that end thereof remote from said one end, said compartment being in communication with said chamber and being of such size as to accommodate said lens housing, said compartment having substantially planar, translucent plates at opposite ends of said compartment alignable with opposite ends of said lens housing when said lens housing is accommodated in said compartment, said pouch when coupled to said adapter enclosing said lens housing and providing a sterile environment for said lens housing.

2. The apparatus according to claim 1 wherein said pouch has a wall defining said chamber, said compartment being sealed to and projecting beyond said wall.

3. The apparatus according to claim 1 wherein said pouch has a wall defining said chamber, a portion of said wall being stiffened between said compartment and said opening to minimize outward bulging of said portion of said wall outward of said chamber.

4. The apparatus according to claim 1 wherein said pouch has a wall defining said chamber, a portion of said wall being stiffened at a zone adjacent said opening in a position to underlie said adapter when said pouch is coupled to said adapter.

5. The apparatus according to claim 4 including first retaining means carried by said wall within said chamber and cooperable with second retaining means carried by said microscope when said pouch is coupled to said adapter, said first and second retaining means being operable releasably to maintain said zone of said pouch in said position when said pouch is coupled to said adapter.

6. A sterilizable pouch for use with an ophthalmoscopic microscope having a lens housing and at least one lens carried by said housing, said pouch having a wall defining a chamber, said chamber having an opening at one end thereof but otherwise being closed at all times; an elastically stretchable support secured to said wall and encircling said opening for coupling said pouch to said microscope; and means forming a compartment in communication with but projecting beyond said chamber and sealed to said wall, said compartment being of such size and shape as wholly to accommodate therein the lens housing and the lens carried thereby.

7. The pouch according to claim 6 wherein said compartment has opposite ends, each of said ends including a translucent, substantially flat plate.

8. The pouch according to claim 7 wherein said opposite ends of said compartment are coaxial.

9. The pouch according to claim 8 wherein said opposite ends of said compartment are transparent.

10. The pouch according to claim 6 wherein said opening has an area resiliently enlargeable in response to stretching of said support.

11. The pouch according to claim 6 wherein said wall includes first stiffening means in a position between said compartment and said opening.

12. The pouch according to claim 11 wherein said wall includes second stiffening means in a position between said first stiffening means and said opening.

13. The pouch according to claim 12 wherein said second stiffening means is circular.

14. The pouch according to claim 11 wherein said first stiffening means is quadrangular.

* * * * *